(12) United States Patent
Kingsman et al.

(10) Patent No.: US 6,235,522 B1
(45) Date of Patent: May 22, 2001

(54) LENTIVIRAL VECTORS

(75) Inventors: Alan John Kingsman; Susan Mary Kingsman, both of Oxon (GB)

(73) Assignee: Oxford Biomedica (UK) Limited, Oxford (GB)

(*) Notice: Subject to any disclaimer, the term of this patent is extended or adjusted under 35 U.S.C. 154(b) by 0 days.

(21) Appl. No.: 09/284,011

(22) PCT Filed: Oct. 17, 1997

(86) PCT No.: PCT/GB97/02858

§ 371 Date: Apr. 5, 1999

§ 102(e) Date: Apr. 5, 1999

(87) PCT Pub. No.: WO95/32300

PCT Pub. Date: Nov. 30, 1995

(30) Foreign Application Priority Data

Oct. 17, 1996 (GB) .................................... 9621680

(51) Int. Cl.[7] .............................. C12N 15/00; C12N 7/00
(52) U.S. Cl. ..................... 435/320.1; 435/235.1; 435/455; 435/456; 526/24.1
(58) Field of Search ................... 435/320.1, 455, 435/456, 235.1; 536/24.1; 424/93.2

(56) References Cited

U.S. PATENT DOCUMENTS 5,604,114 * 2/1997 Haseltine et al. ................... 435/69.1

FOREIGN PATENT DOCUMENTS

| WO 92/21750 | 12/1992 | (WO) . |
| WO 95/30755 | 11/1995 | (WO) . |
| WO 95/32300 | 11/1995 | (WO) . |
| WO 96/14332 | 5/1996 | (WO) . |
| WO 96/28563 | 9/1996 | (WO) . |
| WO 96/37623 | 11/1996 | (WO) . |
| WO 97/48277 | 12/1997 | (WO) . |

OTHER PUBLICATIONS

Chang et al. Human Immunodeficiency Viruses Containing Heterologous Enhancer/Promoters are Replication Competent and Exhibit Different Lymphocyte Tropisms. Journal of Virology, vol. 67, pp. 743–752, Feb. 1993.*

Verma et al. Gene Therapy–Promises, Problems, and Prospects. Nature, vol. 389, pp. 239–242, Sep. 18, 1997.*

Eck et al. Gene–Based Therapy. Goodman & Gilman's The Pharmacological Basis of Therapeutics, 9th Edition, Chapter 5, 1996.*

Paulus et al, "Self–Contained, Tetracycline–Regulated Retroviral Vector System for Gene Delivery to Mammalian Cells", *Journal of Virology*, vol. 70, No. 1, Jan. 1996, pp. 62–67.

Parolin et al, "Use of cis–and trans–Acting Viral Regulatory Sequences to Improve Expression of Human Immunodeficiency Virus Vectors in Human Lymphocytes", *Virology*, vol. 222, Aug. 15, 1996, pp. 415–422.

* cited by examiner

*Primary Examiner*—Deborah J. R. Clark
*Assistant Examiner*—Eleanor Sorbello
(74) *Attorney, Agent, or Firm*—Nixon & Vanderhye P.C.

(57) ABSTRACT

Retroviral vector particles capable of infecting and transducing non-dividing mammalian target cells, which vector particles may be based on letiviruses such as HIV and which have an RNA genome constructed so as to provide in the DNA provirus a non-lentiviral expression control element in the 5'LTR of the provirus.

15 Claims, 4 Drawing Sheets a) Lentivirus genome b) LLD vector

=LENTIVIRAL SEQUENCES

=HETEROLOGOUS SEQUENCES

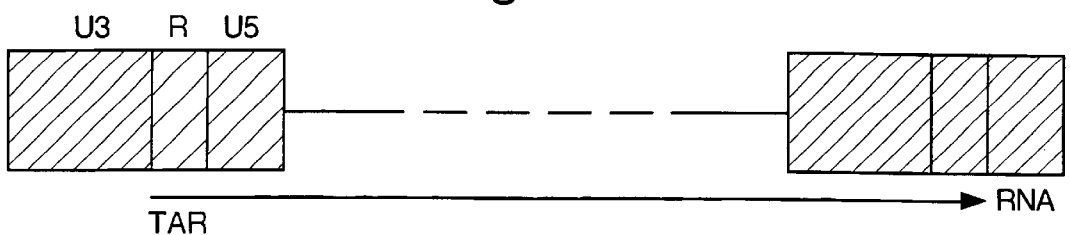
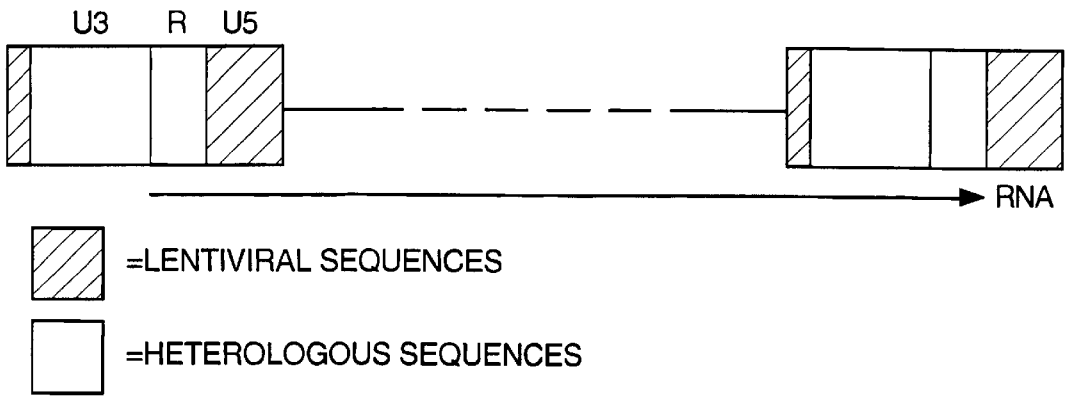

Fig.6.
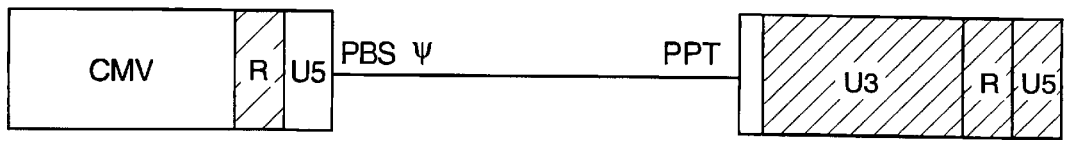
HIV
MLV
↓ Transcription
Viral RNA
↓ Reverse transcription
Proviral DNA
NON-LENTIVIRAL SEQUENCES eg. MLV ▨
LENTIVIRUS eg. HIV ☐

LENTIVIRAL VECTORS

This invention relates to retroviral vector particles and to DNA constructs encoding RNA genomes for retroviral vectors. In particular it relates to retroviral vectors capable of transferring genetic material to non-dividing or slowly-dividing cells.

There has been considerable interest, for some time, in the development of retroviral vector systems based on lentiviruses, a small subgroup of the retroviruses. This interest arises firstly from the notion of using HIV-based vectors to target anti-HIV therapeutic genes to HIV susceptible cells and secondly from the prediction that, because lentiviruses are able to infect non-dividing cells (Lewis & Emerman 1993 J.Virol. 68, 510), vector systems based on these viruses would be able to transduce non-dividing cells (e.g. Vile & Russel 1995 Brit. Med. Bull. 51, 12). Vector systems based on HIV have been produced (Buchschacher & Panganiban 1992 J.Virol. 66, 2731)) and they have been used to transduce CD4+ cells and, as anticipated, non-dividing cells (Naldini et al, 1996 Science 272, 263). However, in general gene transfer efficiencies are not as high as with comparable murine retrovirus vector systems.

HIV-based vectors produced to date result in an integrated provirus in the transduced cell that has HIV LTRs at its ends. This limits the use of these vectors as the LTRs have to be used as expression signals for any inserted gene unless an internal promoter is used. The use of internal promoters has significant disadvantages (see later). HIV and other lentiviral LTRs have virus-specific requirements for gene expression. For example, the HIV LTR is not active in the absence of the viral Tat protein (Cullen 1995 AIDS 9, S19). It is desirable, therefore, to modify the LTRs in such a way as to change the requirements for gene expression. In particular tissue specific gene expression signals may be required for some gene therapy applications or signals that respond to exogenous signals may be necessary. In murine retroviruses this is often achieved simply by replacing the enhancer-like elements in the U3 region of the MLV LTR by enhancers that respond to the desired signals. This is not feasible with viruses such as HIV because within the U3 and R regions of their LTRs are sequences, known as IST and TAR, which may inhibit gene expression and may or may not be responsive to Tat protein when heterologous, perhaps tissue specific, control sequences are inserted in the U3 region (Cullen 1995 AIDS 9, S19; Alonso et al, 1994 J. Virol. 68, 6505; Ratnasabapathy et al, 1990 4, 2061;Sengupta et al, 1990 PNAS 87, 7492; Parkin et al, 1988 EMBO.J 7, 2831)). Even if the signals are responsive it is undesirable to have to supply Tat as it further complicates the system and Tat has some properties of oncoproteins (Vogel et al, 1988 Nature 335, 606). Overall, these considerations mean that the R region of HIV and other lentivirus vectors must be removed if effective expression from non-lentiviral sequences in the LTR is to be achieved.

We have described previously in PCT/GB96/01230 a method for replacing both the U3 and R regions of retroviral vector genomes. The observation that R regions could be replaced was surprising as it was previously believed that these were specific to the virus that is providing the reverse transcriptase for the conversion of the RNA viral genome to the preintegrated form of the proviral DNA. PCT/GB 96/01230 describes in particular retrovirus vectors for delivering therapeutic genes whose expression in the target cell is HIV-dependent. Delivery to non-dividing or slowly-dividing cells is not addressed, and application of the invention to HIV or any other lentivirus-based vectors is not addressed.

The general approach described in PCT/GB 96/01230 now provides a means of producing an HIV-based vector with the U3 enhancer and R regions replaced by any sequence of choice providing that appropriate polyadenylation and transcription termination regions are included in the R region.

The present invention provides in one aspect a retroviral vector particle based on a first retrovirus, said retroviral vector particle capable of infecting and transducing non-dividing mammalian target cells, said retroviral vector particle comprising a packagable RNA genome capable of being inserted into a target cell genome when in the form of a DNA provirus, said RNA genome comprising sequences which provide in the DNA provirus:

a) a non-lentiviral expression control element located in the 5' long terminal repeat (LTR) of the provirus in place of the promoter function of the first retrovirus; and b) a selected gene or genes under transcriptional control of the non-lentiviral expression control element in a), the selected gene or genes located between the LTRs.

In another aspect, the invention provides a DNA construct encoding the packagable RNA genome for the retroviral vector particle described herein, operably linked to a promoter. In the DNA construct, the selected gene or genes may be present, or be absent in which case the construct has an insertion site e.g. a restriction enzyme site, at which the selected gene or genes may be inserted.

In a further aspect, the invention provides a retroviral vector particle production system comprising a host cell transfected or transduced with a DNA construct as described herein, said system capable of producing retroviral vector particles as described herein.

In yet another aspect, the invention provides a retroviral vector particle production system comprising a set of nucleic acid sequences encoding the components of a retroviral vector particle as described herein.

In still further aspects, the invention provides the use of the retroviral vector particles described herein for gene therapy and in the preparation of a medicament for use in gene therapy; and a method of performing gene therapy on a target cell which method comprises infecting and transducing the target cell using a retroviral vector particle as described herein. The invention further provides transduced target cells resulting from these uses and methods. The invention thus provides a gene delivery system for use in medicine.

That the vector particle according to the invention is "based on" a first retrovirus means that it is derived from that retrovirus. The genome of the vector particle comprises components from that retrovirus as a backbone. The vector particle as a whole contains essential vector components compatible with the RNA genome, including reverse transcription and integration systems. Usually these will include gag and pot proteins derived from the first retrovirus.

Preferably, the first retrovirus is a lentivirus which provides the ability to infect and transduce non-dividing cells. During the infection process, lentiviruses form a pre-integration complex in the target cell cytoplasm containing integrase, core proteins and the proviral DNA. The complex is able to pass across the nuclear membrane of the target cell, by is means of signal sequences in the proteins. Other retroviruses either lack the proteins, or have the proteins but without the appropriate signal sequences. It is therefore expected to be possible in principle to introduce into retroviruses other than lentiviruses the ability to infect non-dividing cells.

Examples of lentiviruses are HIV, SIV, FIV, BLV, EIAV, CEV and visna virus. Of these, HIV and SIV are presently best understood. However, preferred for use in gene therapy would be a non-immunodeficiency lentivirus because the immunodeficiency viruses inevitably bring with them safety considerations and prejudices.

The non-lentiviral expression control element will usually be a promoter which term includes known promoters, in part or in their entirety, which may be constitutively acting or it may be a regulated promoter inducible only under certain conditions e.g. in the presence of a regulatory protein. This enables expression of the selected gene or genes to be restricted e.g. to particular cell types or to cells in which a particular exogenous signal is present. For example, heavy metal induction of a gene could be achieved by using components of the metallothionein promoter. Expression control by a steroid hormone may be another useful approach. Brain-specific, stem cell specific or tumour-specific gene expression signals might alternatively be used.

The non-lentiviral promoter replaces the lentiviral-protein dependent promoter function of the lentiviral 5' LTR. For HIV, this means that the 5' LTR is no longer responsive to the HIV Tat protein. Tat acts on the TAR region of R; in an HIV-based vector according to the invention functional TAR sequences are therefore absent in order to avoid reductions of translation by the TAR structure. Enhancer sequences contained in the HIV U3 regions are also preferably excluded. A straightforward way to achieve the desired vector LTRs is therefore to replace the lentiviral R regions and as far as possible the U3 regions, but leaving essential lentiviral sequences present such as a short sequence of the U3 region necessary for integration.

As will be evident, in order to function as a vector the retroviral vector particle according to the invention will need to have a reverse transcription system (compatible reverse transcriptase and primer binding sites) and an integration system (compatible integrase and integration sites) allowing conversion to the provirus and integration of the double-stranded DNA into the host cell genome. Additionally, the vector genome will need to contain a packaging signal. These systems and signals are described in more detail below in the Examples and will generally be provided by the first retrovirus, on which the vector is based. It will be evident also that although the vector according to the invention is based on a particular first retrovirus, this may be a genetically or otherwise (e.g. by specific choice of packaging cell system) altered version of the retrovirus. For example, portions of the first retroviral genome not required for its ability to be packaged, undergo reverse transcription and integrate, can be excluded. Also, the vector system can be altered e.g. by using different env genes to alter the vector host range and cell types infected or transduced.

It may be advantageous to include further elements of the retrovirus on which the vector is based. For HIV this might include functional rev and RRE sequences, enabling efficient export of RRE- containing RNA transcripts of the vector genome from the nucleus to the cytoplasm of the target cell.

The selected gene or genes under the control of the promoter in the proviral 5' LTR is or are chosen according to the effect sought to be achieved. For gene therapy purposes there will be at least one therapeutic gene encoding a gene product which is active against the condition it is desired to treat or prevent. Alternatively or additionally, there may be a selected gene which acts as a marker by encoding a detectable product. Therapeutic genes may encode for example an anti-sense RNA, a ribozyme, a transdominant negative mutant of a target protein, a toxin, a conditional toxin, an antigen that induces antibodies or helper T-cells or cytotoxic T-cells, a single chain antibody or a tumour suppresser protein.

The selected gene or genes between the LTRs in the DNA provirus is or are under the transcriptional control of the promoter in the 5' LTR but not otherwise operably linked to any other promoter from the vector. Thus, expression of the selected gene or genes is in a single transcription unit. However, as will be discussed below there may be additional transcription units within the vector genome. These should not interfere with the transcription unit containing the selected gene or genes.

Where two or more genes are present and under transcriptional control of the 5' LTR promoter, there may be an internal ribosome entry site (IRES) e.g. from picornaviral RNA, to allow both genes to be separately translated from a single transcript. Retroviruses incorporating IRES sequences have been constructed by others.

A further gene or genes may also be present under the control of a separate promoter. Such a gene may encode for example a selectable marker, or a further therapeutic agent which may be among the therapeutic agents listed above. Expression of this gene may be constitutive; in the case of a selectable marker this may be useful for selecting successfully transfected packaging cells, or packaging cells which are producing particularly high titers of the retroviral vector particles. Alternatively or additionally, the selectable marker may be useful for selecting cells which have been successfully infected with the retroviral vector and have the provirus integrated into their own genome.

One way of performing gene therapy is to extract cells from a patient, infect the extracted cells with a retroviral vector and reintroduce the cells back into the patient. A selectable marker may be used to provide a means for enriching for infected or transduced cells or positively selecting for only those cells which have been infected or transduced, before reintroducing the cells into the patient. This procedure may increase the chances of success of the therapy. Selectable markers may be for instance drug resistance genes, metabolic enzyme genes, or any other selectable markers known in the art.

However, it will be evident that for many gene therapy applications of retroviral vectors, selection for expression of a marker gene may not be possible or necessary. Indeed expression of a selection marker, while convenient for in vitro studies, could be deleterious in vivo because of the inappropriate induction of cytotoxic T lymphocytes (CTLs) directed against the foreign marker protein. Also, it is possible that for in vivo applications, vectors without any internal promoters will be preferable. The presence of internal promoters can affect for example the transduction titres obtainable from a packaging cell line and the stability of the integrated vector. Thus, single transcription unit vectors, which may be bi-cistronic or poly-cistronic, coding for one or two or more therapeutic genes, may be the preferred vector designed for use in vivo.

It will be evident that the term "gene" is used loosely here, and includes any nucleic acid coding for the desired polypeptide. Usually, the genes delivered by the vector according to the invention will be cDNAs.

It is desirable for the purposes of gene therapy that the retroviral vector genome does not encode any unnecessary polypeptides, that is any polypeptides that are not required for achieving the effect the vector is designed for. In any case, the retroviral vector will be replication defective. Thus, it is necessary to exclude from the vector genome full length gag-pol or env coding regions, or preferably both. This has the dual purpose of avoiding unwanted immune responses directed against the foreign viral proteins, and reducing the possibility of a replication competent retrovirus being generated by recombination.

The retroviral vector particle according to the invention will also be capable of infecting and transducing cells which are slowly-dividing, and which non-lentiviruses such as MLV would not be able to efficiently infect and transduce. Slowly-dividing cells divide once in about every three to four days. Mammalian non-dividing and slowly-dividing cells include brain cells, stem cells, terminally differentiated macrophages, lung epithelial cells and various other cell types. Also included are certain tumour cells. Although tumours contain rapidly dividing cells, some tumour cells especially those in the centre of the tumour, divide infrequently.

DNA constructs encoding the vector genome described herein are preferably linked to a high efficiency promoter such as the CMV promoter. Other high efficiency promoters are known. This gives rise to a high level of expression of the vector RNA in the host cell producing the retroviral vector particles.

Suitable host or producer cells for use in the invention are well known in the art. Many retroviruses have already been split into replication defective genomes and packaging components. For those which have not the technology is available for doing so. The producer cell encodes the viral components not encoded by the vector genome such as the gag, pol and env proteins. The gag, pol and env genes may be introduced into the producer cell and stably integrated into the cell genome to give a packaging cell line. The retroviral vector genome is then introduced into the packaging cell line by transfection or transduction to create a stable cell line that has all of the DNA sequences required to produce a retroviral vector particle. Another approach is to introduce the different DNA sequences that are required to produce a retroviral vector particle e.g. the env coding sequence, the gag-pol coding sequence and the defective retroviral genome into the cell simultaneously by transient triple transfection (Landau & Littman 1992 J. Virol. 66, 5110; Soneoka et al 1995).

The strategy according to the invention has several advantages in addition to those already described. Firstly, by making use of the 5' LTR as the expression signal for a therapeutic transcription unit it is possible to make this vector genome a single transcription unit genome for both production and expression in the transduced cell. This avoids the need for internal promoters between the LTRs. The unpredictable outcome of placing additional promoters within the retroviral LTR transcription unit is well documented (Bowtell et al, 1988 J.Virol. 62, 2464; Correll et al, 1994 Blood 84, 1812; Emerman and Temin 1984 Cell 39, 459; Ghattas et al, 1991 Mol.Cell.Biol. 11, 5848; Hantzopoulos et al, 1989 PNAS 86, 3519; Hatzoglou et al, 1991 J.Biol.Chem 266, 8416; Hatzoglou et al, 1988 J.Biol.Chem 263, 17798; Li et al, 1992 Hum.Gen.Ther. 3, 381; McLachlin et al, 1993 Virol. 195, 1; Overell et al, 1988 Mol.Cell Biol. 8,1803; Scharfman et al, 1991 PNAS 88, 4626; Vile et al, 1994 Gene Ther 1, 307; Xu et al, 1989 Virol. 171, 331; Yee et al, 1987 PNAS 84, 5197). The factors involved appear to include the relative position and orientation of the two promoters, the nature of the promoters and the expressed genes and any selection procedures that may be adopted. The presence of internal promoters can affect both the transduction titers attainable from a packaging cell line and the stability of the integrated vector. Loss of gene expression following transduction can be caused both by provirus deletions and reversible epigenetic mechanisms of promoter shutdown. In addition, data from tissue culture studies can often have no bearing on the performance of the vectors in vivo. These considerations suggest that simple retroviral vectors containing a single LTR promoter are likely to be promising vectors for gene therapy (Correll et al 1994 Blood 84, 1812). In addition, with the development of bi-cistronic vectors using only one promoter (Adam et al, 1991 J.Virol 65,4985) it will also be possible to produce single transcription unit vectors coding for two or more therapeutic genes, with correspondingly greater efficacy.

The second advantage of removing the HIV expression signals within the U3 and R regions is that these signals are subject to a number of external influences on their activity. It is known that the HIV promoter can be activated by a variety of agents such as UV, stress, other viruses etc. (Peterlin 1992 in Human Retroviruses ed. Cullen. IRL Press) which makes the transcriptional status of the vector genome difficult to control. Removal of these sequences will ensure greater control over the therapeutic gene.

In the attached figures:

FIG. 1 shows a general scheme for vectors according to the invention;

FIG. 2 shows a generalised HIV-based vector genome according to the invention;

Figure 3:
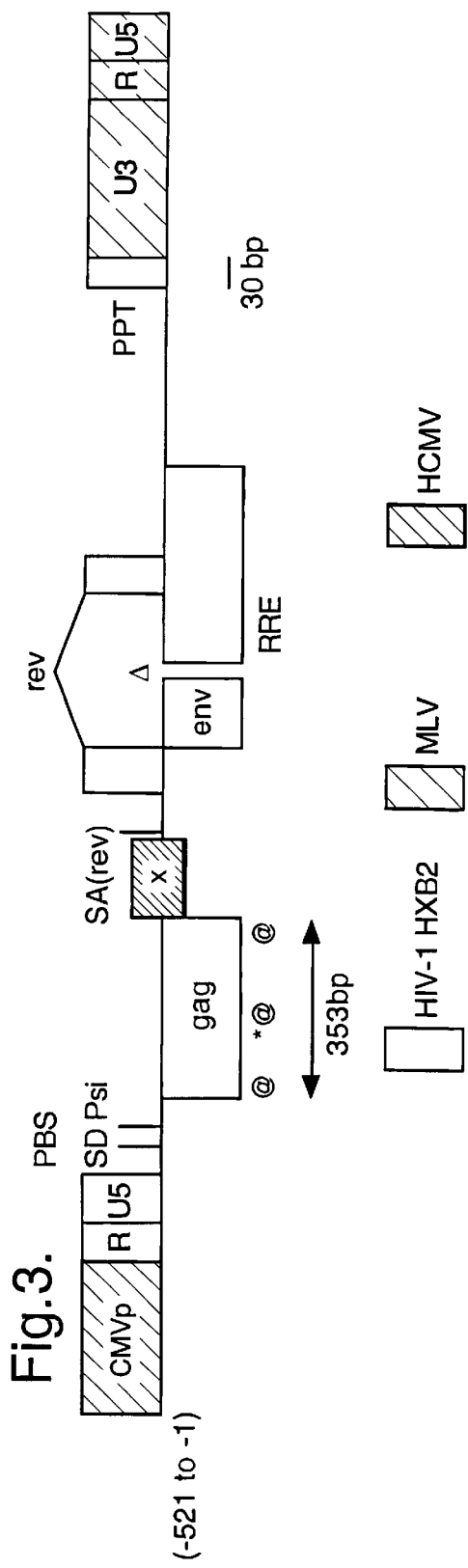
FIG. 3 shows the HIV-based vector genome described in Example 1.

FIG. 6 further shows the principle of vectors according to the invention.

The invention is outlined in FIG. 1. The vector system is designated Lentiviral LTR-Deleted (LLD) vector. It comprises a DNA molecule in which a CMV or other high efficiency promoter is used to drive the expression of the vector RNA in a producer cell. This strategy is analogous to the HIT vector system (Soneoka et al, 1995 Nucl.Acids Res. 23, 628). The producer cell will have been engineered to produce compatible lentiviral structural proteins and enzymes. It will be, therefore, what is known as a vector packaging cell. The producer DNA can be used as an autonomous plasmid that either does or does not replicate or it can be integrated into the producer cell genome. All of these strategies are known in the field (Soneoka et al, 1995 Nucl.Acids Res. 23, 628; Miller and Rossman 1989 Bio-Tech. 7, 980; Miller 1990 Hum.Gene Ther. 1, 5). The producer DNA for the vector genome may contain at least the following contiguous components: A high efficiency promoter, a non-lentiviral R region that either comes from another retrovirus or is completely synthetic, all or part of the lentiviral U5 region that contains sequences required for integration by the lentiviral integrase and sequences necessary for efficient reverse transcription, packaging signals that are recognized by the packaging components of the producer cell, an internal region that might contain genes including therapeutic or reporter genes or selectable markers and associated expression signals (in addition the internal region might contain components of systems for ensuring efficient RNA splicing and transport), a second strand primer site from the lentivirus, a short sequence of 30–100 nucleotides from the lentivirus U3 region that is required for efficient integration by the lentivirus integrase, a heterologous promoter that might confer tissue specificity of gene expression or regulation by an exogenous signal so that a therapeutic gene can be expressed appropriately, an R region that is identical to the first R region together with transcription termination and polyadenylation signals required to produce a vector RNA with terminal R regions. This producer DNA produces an RNA molecule that is packaged by the lentiviral packaging system. The resulting vector particles will deliver that RNA to a susceptible cell, the RNA will be converted to DNA by the lentiviral reverse transcriptase and it will be integrated into the cells genome by the lentiviral integrase. The resulting provirus will have the CMV promoter component of the producer DNA replaced by the short lentiviral sequence from the end of the lentiviral U3 region and the heterologous promoter that may confer tissue specific or regulated gene expression. Because the lentiviral R region has been entirely replaced there are no inhibitory TAR sequences in the integrated vector genome.

EXAMPLES

Example 1

An HIV-based LLD Vector with the MLV U3 Promoter and MLV R Regions

Figure 4:
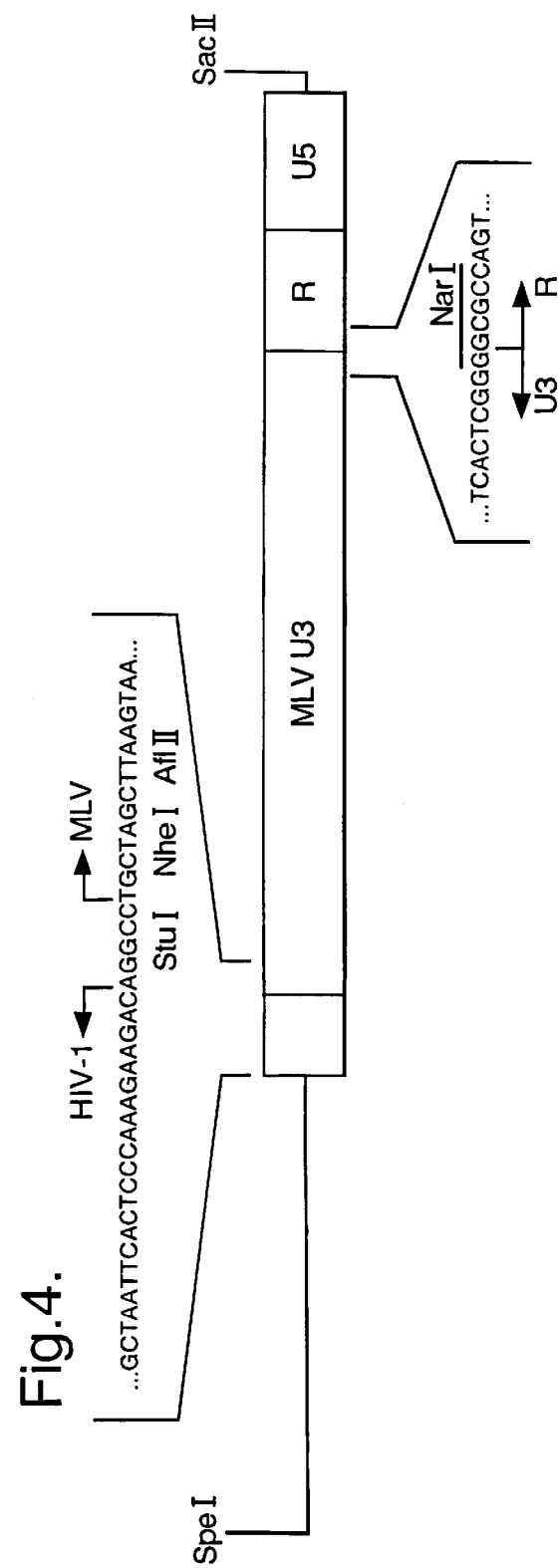
FIG. 4 shows in more detail the structure of the 3' LTR for the vector in FIG. 3.

The structure of a general HIV LLD vector system is shown in FIG. 2. This example is shown in FIGS. 3 and 4. It is constructed as follows. The minimal requirements for HIV reverse transcription are the primer binding site (PBS) to initiate the negative strand DNA synthesis, the polypurine tract (PPT) to initiate the positive DNA synthesis, and identical 5' and 3' R sequences to allow the first template switch. The incorporation of the PBS and PPT from HIV-1 into the vector and the R sequences from MLV into both LTRs is therefore required. As secondary structure within the 5' U5 region might be important for reverse transcription, the U5 region in the 5' LTR is from HIV-1. For the U5 region at the 3' LTR, the U5 from HIV-1 was used to make sure correct termination of transcription occurred at the R-U5 border. However, any termination signals could be used. For efficient integration, 30 nucleotides at the 5' end of the HIV-1 U3 at the 3' LTR were incorporated.

In order for the MLV U3 element to appear in the 5' LTR after reverse transcription, it must be in the 3' LTR of the viral RNA. The whole MLV U3 except 30 bps of the 5' end replaced the HIV-1 U3. The 3' LTR of the vector was designed to contain several convenient restriction sites, so that the MLV U3 can be easily replaced by other heterologous promoters (FIG. 4). Any heterologous promoters will be amplified by PCR with primers containing StuI and NarI sites at each end and will be used to replace the MLV U3. Not only StuI but also NheI and AflII may be used at the 5' end of the promoter cassettes. NarI(GGCGCC) is located on the junction between the promoter and R, so that the transcription start site from the heterologous promoter can be preserved. The MLV U3 sequences between XbaI and NarI contains the basic promoter elements including TATA box, GC box, and CAAT box. Therefore the MLV enhancer can be replaced by any other enhancers as a StuI (or NheI or AflIII) - XbaI cassettes.

For efficient packaging 353 nucleotides of gag is known to be sufficient (Srinivasakumar et al, 1996 CSH Retrovirus Meeting abstract). The 353 nucleotides of gag sequences corresponds to the sequences from 790 to 1144, within this three ATG's (790, 834, 894) were removed by mutation. In addition a polycloning site is located downstream of gag.

In order to achieve efficient export of RNA species encoded by HIV genome, rev and RRE are required. They are included in the LLD vector and correspond to sequences 5861 to 6403 and 7621 to 9085 from is HIV-1 (HXB2). Tat coding sequence is not present in the vector.

Details of Construction of the Producer DNA

A. 5' Structure (All HIV-1 Coordinates are from HXB from the Loa Alamos Sequence Database and MoMLV Sequences are from Shinnick et al 1981 Nature 293, 543)

The 5' half of the vector contains the hybrid 5' LTR (CMV promoter-MLV R -HIV-1 U5), HIV-1 PBS, and HIV-1 packaging signal. This will be constructed by recombination PCR. One of the templates for the PCR, pHIVdge2, is an HIV-1 proviral DNA which has a mutation created by filling-in and religation at the ClaI site (831) and a deletion between NdeI(6403) and BglII(7621). The junction between MLV R and HIV-1 U5 is created by two primary PCR reactions (using the primer NIT1 and NIT2; NIT3 and NIT4) and a secondary PCR reaction (using the primers NIT1 and NIT4). The PCR product is inserted into pBluesriptKS+ (STRATAGEN) at KpnI and XhoI site (Construct A1). In order to mutate three ATGs in the gag region, the primers contain mutated codons.

NIT1: 5'-ccgggtacccgtattcccaataaagcctcttgctgtttgca-3' (SEQ ID NO: 1)

NIT2: 5'-ctacgatctaattctcccccgcttaatactgacgctctcgcacctatctc-3' (SEQ ID NO 2)

NIT3: 5'-gcggggagaattagatcgtagggaaaaaattcggttaaggccag ggggaaagaaaaaatataaa ttaaaacatatagtttggg-3' (SEQ ID NO: 3)

NIT4: 5'-gaattctcgaggcgtgctgtgcttttttctatc-3' (SEQ ID NO: 4)

The CMV promoter—MLV R fragment is amplified by PCR from pRV109 (Soneoka et al, 1995) to contain KpnI sites at both ends using the PCR primers NIT5 and NIT6 and inserted into construct A1 to produce construct A2.

NIT5: 5'-gtaggtacccgttacataacttacggtaaatg-3' (SEQ ID NO: 5)

NIT6: 5'-agaggctttattgggaatacg-3' (SEQ ID NO: 6)

B. 3' Structure

The 3' half of the vector genome includes the HIV-1 rev coding region and RRE, PPT, 36 bp of 5' end of HIV-1 U3, and the whole MLV LTR except 30 bp of 5' end. The sequences (5861–6000) are PCR amplified from pHIVdge2 (using NIT7 and NIT8) and are subcloned into pSP64 (PROMEGA) at BamHI and SacI site (Construct B1).

NIT7: 5'-cacggatccactagttggaagcatccaggaagtcagc-3' (SEQ ID NO: 7)

NIT8: 5'-ctctgactgttctgatgagc-3' (SEQ ID NO: 8)

The SacI—SacI fragment (6000–6403 and 7621–9572) from pHIVdge2 is inserted into the above construct to produce construct B2. Finally the HIV-1-MLV hybrid LTR will be created by two primary PCRs (using NIT9 and NIT10 with pHIVdge2 as the template; NIT11 and NIT12 with pLXSN (Accession number M28248; Miller et al, 1989) as the template) and one secondary PCR reaction (using NIT9 and NIT12). The PCR product will be inserted at the XhoI and EcoRI sites in Construct B2 to produce Construct B3.

NIT9: 5'-gagcagcatctcgagacctgg-3' (SEQ ID NO: 9)

NIT10: 5'-tggcgttacttaagctagcaggcctgtcttctttgggagtgttttagc-3' (SEQ ID NO:10)

NIT11: 5'-cccaaagaagacaggcctgctagcttaagtaacgccatttttcc-3' (SEQ ID NO:11)

NIT12: 5'-cctgaattccgcggaatgaaagacccccgctgacg-3' (SEQ ID NO: 12)

C. Complete Vector

The two halves of the vector are combined by inserting the SpeI-SacII fragment from construct B3 into construct A2. The resulting construct, C1, possesses a poly-cloning site; XhoI-SalI-ClaI-HindIII-EcoRV-EcoRI-PstI-SmaI-BamHI-SpeI (underlined sites are unique in the vector). This plasmid is designated pLLD1 and the retroviral vector that it produces is LLD1.

The β-galactosidase gene was then taken from pSP72-lacZ (XhoI-BamHI) and inserted into the construct C1 at SalI and BamHI to produce LLD1-lacZ. This was used to transfect 293T cells together with plasmids providing the HIV gag and pol components (pRV664, FIG. 5) and either a plasmid expressing gp160 from HIV (pRV438 or pSynp160 mn, FIG. 5) or a plasmid expressing the VSVG protein (pRV67, FIG. 5). Any plasmids encoding the same proteins would work equally well. The resulting virus that is produced transduced the lacZ gene to CD4+ Hela cells in the case of virus containing gp160 and to CD4- Hela cells in the case of the VSVG bearing virus. In addition the VSVG bearing virus delivers lacZ to post-mitotic neurones. In each case the expression of the lacZ gene is high, as determined by Xgal staining, and independent of Tat.

Example 2

Other LLD Vectors

Systems similar to that described in Example 1 can be produced from other lentiviruses. These systems avoid using HIV, with its associated perceived risks as a gene delivery system. For example constructions could be designed using sequence information from FIV (Talbott et al, 1989 PNAS 86, 5743), EIAV (Payne et al, 1994 J.Gen.Virol. 75, 425), Visna virus (Sonigo et al 1985 Cell 42, 369; Querat et al, 1990 Virology 175, 434), BIV Garvey et al, 1990 Virology 175, 391) and SIV (Los Alamos sequence database).

Figure Legends

FIG. 2. Example: HIV-based LLD vector.

Superscript H=HIV-derived sequence (could be from any lentivirus).

Superscript M=MLV-derived sequence.

ψ=Packaging site (including gag region).

PBS=Second strand priming site.

INTERNAL=Region containing genes, selectable markers, other promoters or RNA handling systems such as HIV RRE and Rev coding sequences.

FIG. 3. NIT vector genome (Inserts 3789 bp+ backbone 2929bp=6718 bp):

HCMV promoter (−521 to −1) from pRV109.

HIV sequences (552 to 1144; 5861 to 6403; 7621 to 9085) from HXB2.

Genotype; gag-; pol-; env-; rev+; RRE; vif-; vpu-; vpr-; tat-; nef-.

Mutations:

three point mutations to remove ATG (790, 834, 894) (@)

a frameshift mutation by two base insertion (831) (*)

a deletion between NdeI(6403) and BglII (7621) (Δ)

Polycloning site (X); XhoI-SalI-ClaI-EcoRV-EcoRI-PstI-SmaI-BamHI-SpeI; Underlined sites are unique.

Maximal insertion site into the polycloning site: 5997bp.

Backbone; pBluescriptKS+.

Figure 5:
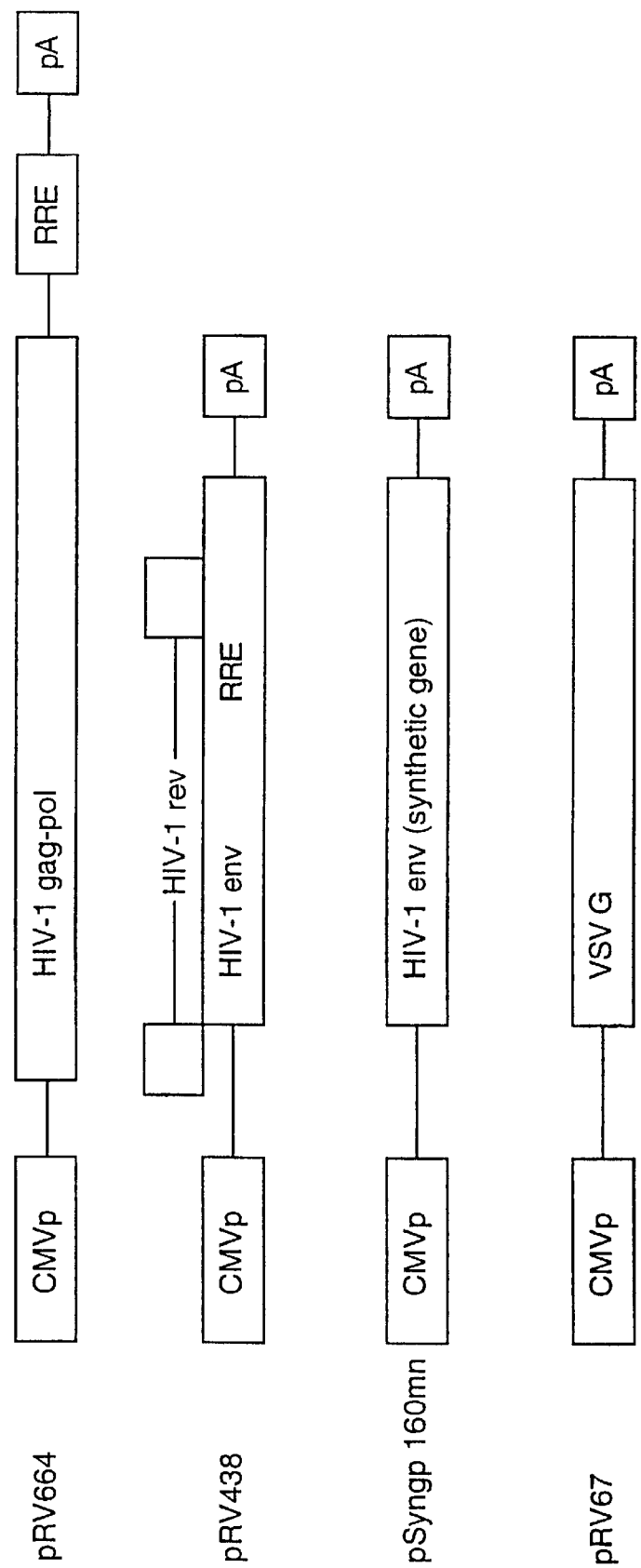
FIG. 5 is a schematic diagram of packaging components.

FIG. 5. Schematic diagram of packaging components.

pRV664 encodes HIV-1 HXB2 gagpol (637-5748) and contains RRE (7720-8054) and its backbone is pCI-neo (PROMEGA).

pRV438 possesses both rev and env from HXB2 (5955-8902) in pSA91 which is a mammalian expression plasmid with CMC promoter. pSYngp 160mn (from B. Seed) is an expression plasmid for HIV-1 MN envelope which was modified to have the optimized codon usage in mammalian cells. pRV67 is a VSV G expression plasmid in pSA91.

What is claimed is:

1. A retroviral vector particle based on a first retrovirus, said retroviral vector particle capable of infecting and transducing non-dividing mammalian target cells, said retroviral vector particle comprising a packagable RNA genome capable of being inserted into a target cell genome when in the form of a DNA provirus, said RNA genome comprising sequences which provide in the DNA provirus:

a) a non-lentiviral R region;

b) a non-lentiviral expression control element located in the 5' long terminal repeat (LTR) of the provirus in place of the promoter function of the first retrovirus;

c) a selected gene or genes under transcriptional control of the non-lentiviral expression control element in b), the selected gene or genes located between the LTRs; and wherein the RNA genome comprises essential lentiviral sequences for integration into the target cell genome.

2. The retroviral vector particle according to claim 1, wherein the first retrovirus is a lentivirus, in which the lentiviral sequence or sequences which provide a 5' lentiviral-protein dependent promoter function in the DNA provirus is/are absent.

3. The retroviral vector particle according to claim 2, wherein the lentivirus on which the vector is based is HIV and functional TAR sequences are absent.

4. The retroviral vector particle according to claim 3, wherein the vector genome further comprises functional rev and RRE sequences, enabling export of RRE containing RNA transcripts of the genome from the nucleus to the cytoplasm of the target cell.

5. The retroviral vector particle according to claim 2, wherein the lentiviral R regions are replaced by non-lentiviral R regions.

6. The retroviral vector particle according to claim 1, wherein the nonlentiviral expression control element is a regulated promoter which is inducible by a non-lentiviral regulatory factor.

7. The retroviral vector particle according to claim 6, wherein the regulated promoter is inducible by a non-viral regulatory factor.

8. The retroviral vector particle according to claim 1, wherein the expression control element comprises an MLV LTR promoter.

9. The retroviral vector particle according to claim 1, wherein the nonlentiviral expression control element comprises non-lentiviral, retroviral U3 and R regions, or functional portions thereof.

10. The retroviral vector particle according to claim 2, wherein the RNA genome comprises a first non-lentiviral R region, a sufficient portion of the lentiviral U5 region for integration and reverse transcription, a primer binding site for first strand reverse transcription, a packaging signal, an internal region containing at least one selected gene, a primer binding site for second strand reverse transcription, a short sequence of the lentivirus U3 region sufficient for integration, a non-lentiviral promoter, and a second R region substantially identical to the first R region.

11. A DNA construct encoding the packagable RNA genome for the retroviral vector particle according to claim 1, operably linked to a promoter.

12. The DNA construct according to claim 11, wherein the promoter is a high efficiency promoter.

13. The DNA construct according to claim 11 or claim 12, wherein the construct has an insertion site at which the selected gene or genes may be inserted.

14. A retroviral vector particle production system comprising a set of nucleic acid sequences encoding the components of a retroviral vector particle according to claim 1.

15. The following phrase to be inserted "with non-lentiviral R regions and portions of non-lentiviral U3 regions" after the phrase "U3 region in a first retroviral vector".

* * * * *